United States Patent [19]
Grillo et al.

[11] Patent Number: 5,470,581
[45] Date of Patent: Nov. 28, 1995

[54] AQUEOUS MALTODEXTRIN AND CELLULOSIC POLYMER FILM COATINGS

[75] Inventors: Susan M. Grillo, Quakertown; Rita M. Steffenino, Green Lane; Diane C. Kunkle; Kathleen Saraceni, both of Lansdale, all of Pa.

[73] Assignee: Berwind Pharmaceutical Services, Inc., West Point, Pa.

[21] Appl. No.: 991,477

[22] Filed: Dec. 15, 1992

Related U.S. Application Data

[63] Continuation of Ser. No. 504,677, Apr. 4, 1990, abandoned.
[51] Int. Cl.$^6$ .................................................. A61K 9/36
[52] U.S. Cl. ........................ 424/479; 424/459; 424/461; 424/463; 424/474; 424/475; 424/480; 424/493; 424/494
[58] Field of Search ................................ 424/459, 461, 424/463, 474, 475, 479, 480, 490

[56] References Cited

U.S. PATENT DOCUMENTS

| | | | |
|---|---|---|---|
| 2,134,714 | 11/1938 | Glassman | 167/65 |
| 3,751,277 | 9/1973 | Small et al. | 106/213 |
| 3,851,574 | 12/1974 | Katz et al. | 426/107 |
| 3,873,694 | 3/1975 | Kanig | 424/127 |
| 3,906,086 | 9/1975 | Guy et al. | 424/20 |
| 3,981,984 | 9/1976 | Signorino et al. | 424/33 |
| 4,095,992 | 6/1978 | Rudolph et al. | 106/213 |
| 4,375,468 | 3/1983 | Dunn | 424/230 |
| 4,533,562 | 8/1985 | Ikegamie et al. | 427/3 |
| 4,543,370 | 9/1985 | Porter et al. | 523/100 |
| 4,596,602 | 6/1986 | Bennett | 127/32 |
| 4,643,894 | 2/1987 | Porter et al. | 424/35 |
| 4,683,256 | 7/1987 | Porter et al. | 524/285 |
| 4,725,441 | 2/1988 | Porter et al. | 424/479 |
| 4,828,841 | 5/1989 | Porter et al. | 424/479 |
| 4,877,629 | 10/1989 | Stypula et al. | 426/302 |
| 4,910,028 | 3/1990 | Bernacchi et al. | 426/93 |
| 4,981,698 | 1/1991 | Cherukuri et al. | 424/48 |
| 4,981,707 | 1/1991 | Morris | 426/93 |
| 5,024,842 | 6/1991 | Edgren et al. | 424/468 |

FOREIGN PATENT DOCUMENTS

| | | | |
|---|---|---|---|
| 2729370 | 1/1978 | Germany | 426/69 |

OTHER PUBLICATIONS

Chemical Abstracts, vol. 100, No. 23, Jun. 4, 1984 abstract 100: 190544j.
Chemical Abstracts, vol. 101, No. 11, Sep. 10, 1984 abstract 101: 89243f.
Chemical Abstracts, vol. 101, No. 17, Oct. 22, 1984 abstract 101: 150241x.
Rowe, "Some Fundamental Properties Of Polymeric Materials And Their Application In Film Coating Formulations" Int. J. Pharm. Tech & Prod, Mfr., (3) 1982.
Rowe & Forse, "The Effect Of Polymer Molecular Weight On The Incidence Of Cracking And Splitting On Film Coated Tablets", COMMUNICATIONS, J. Pharm. Pharmacol, p. 32, Jan. 1980.

Primary Examiner—Thurman K. Page
Assistant Examiner—James Spear
Attorney, Agent, or Firm—John F. A. Earley; John F. A. Earley, III

[57] ABSTRACT

A method of coating substrates such as pharmaceutical tablets, food and confectionery forms, agricultural seeds and the like, with a protective film comprises the steps of mixing a cellulosic polymer, maltodextrin, and a plasticizer into water to form an aqueous coating suspension, spraying an effective amount of said coating suspension onto said substrates to form a film coating on said substrates, and drying the film coating on said substrates. Optionally, a detackifier, a secondary film former, a flow aid, and/or a colorant may be dispersed into the coating suspension before applying the coating suspension to the substrates. A dry powder edible film coating composition for use in pharmaceuticals, food and confectionery forms, agricultural seeds, and the like, comprises a dry mixture of a cellulosic polymer, maltodextrin, and a plasticizer. Optionally, the dry coating composition may include a detackifier, a secondary film former, a flow aid, and/or a colorant.

62 Claims, 4 Drawing Sheets

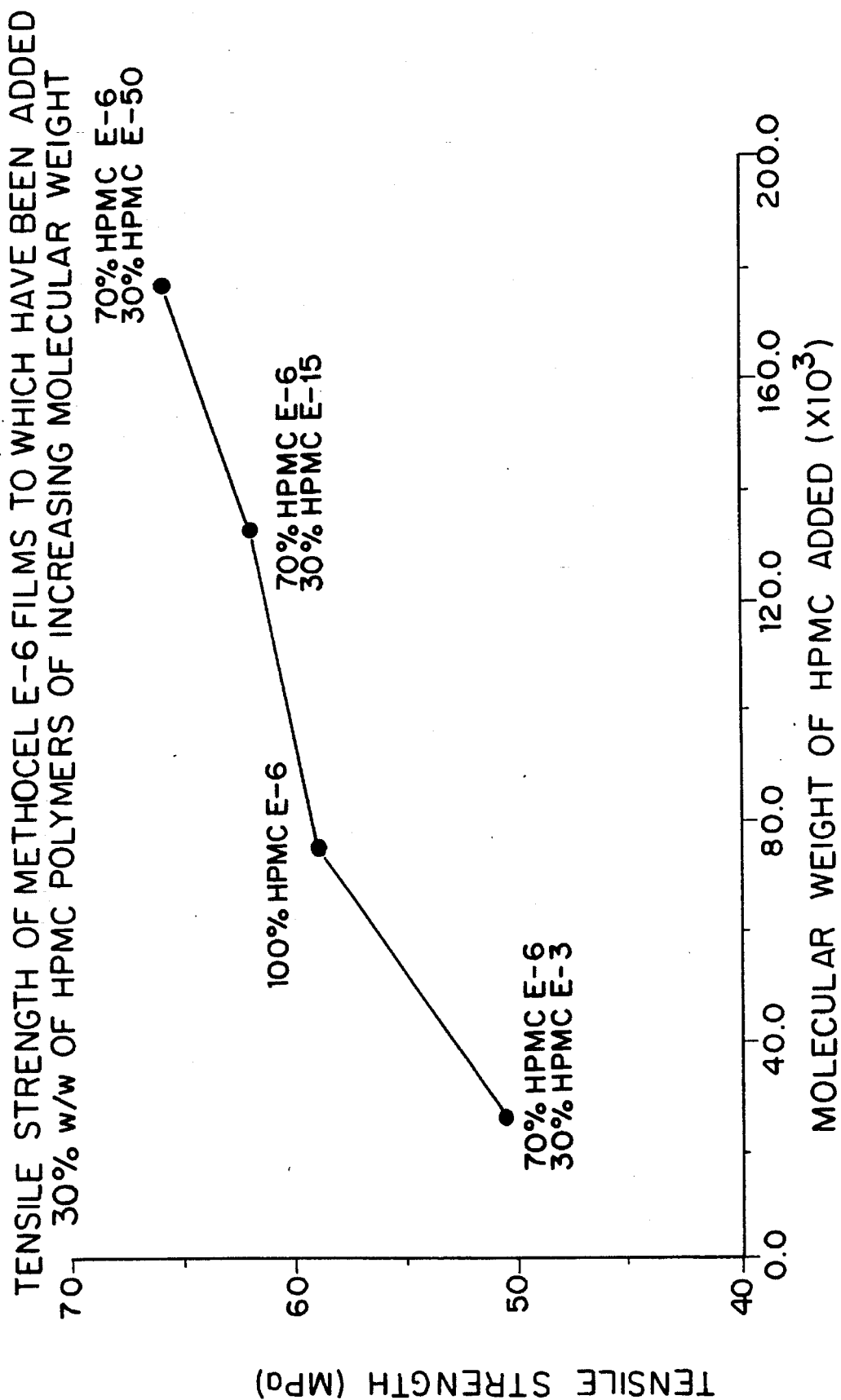

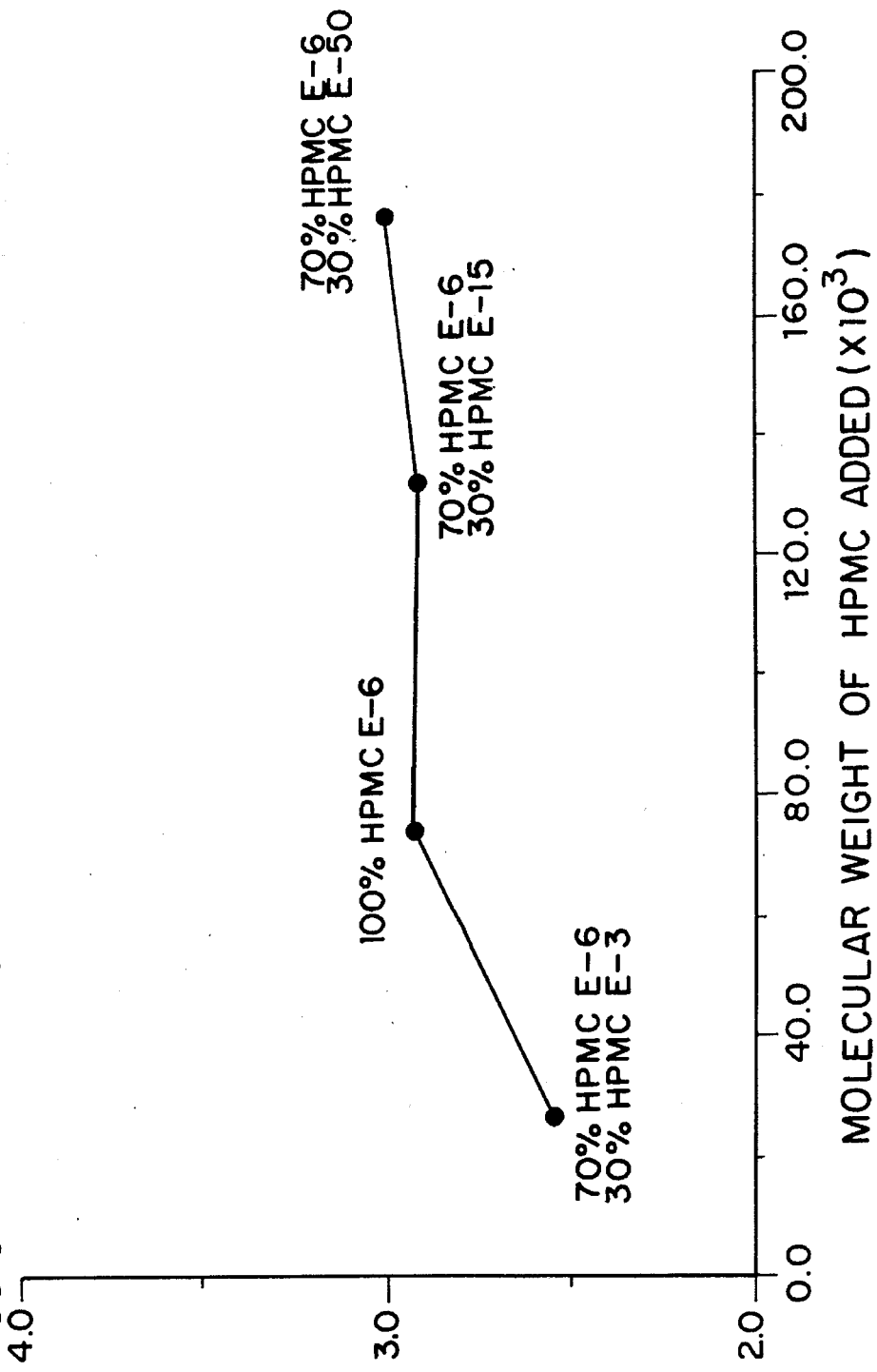

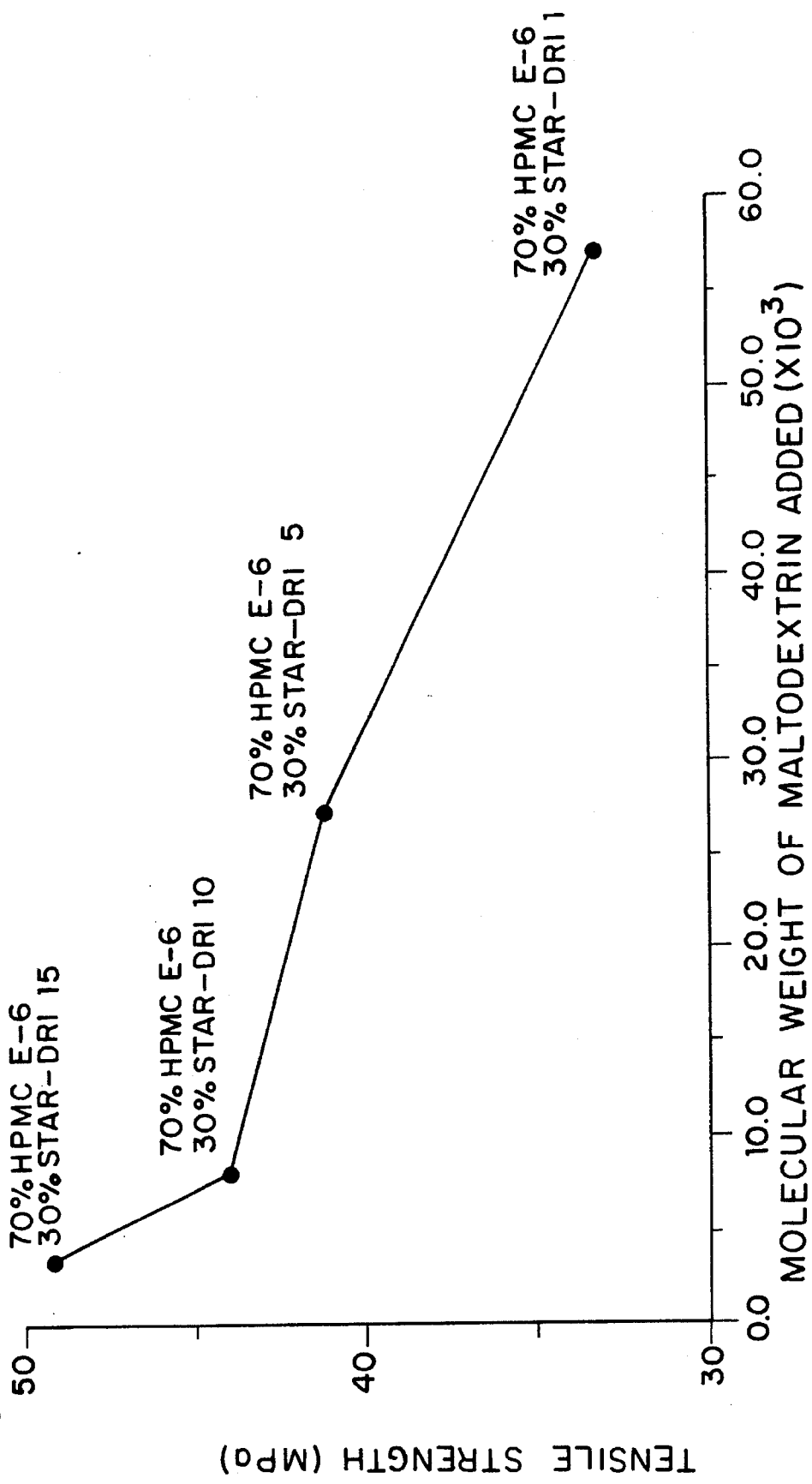

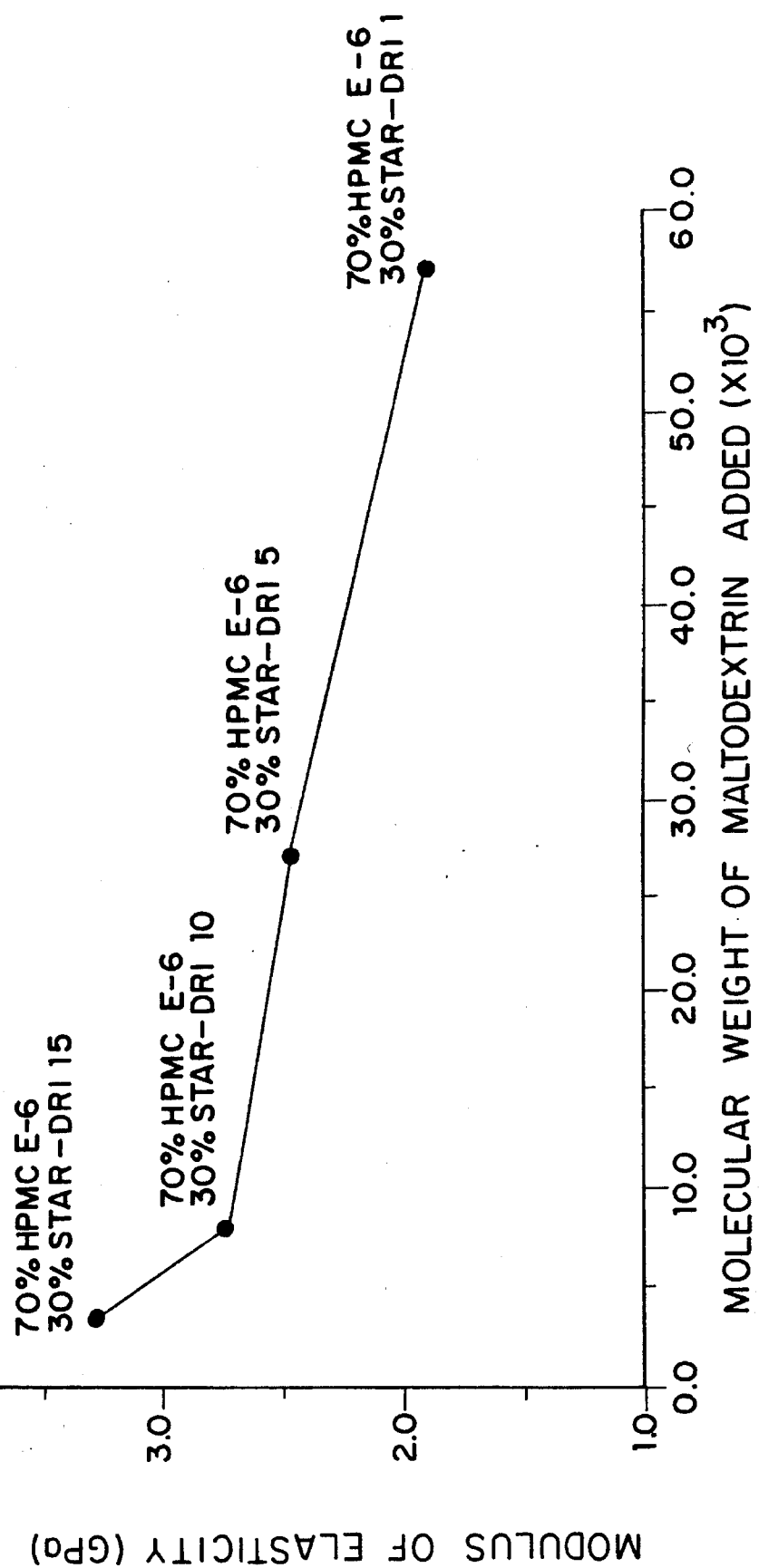

AQUEOUS MALTODEXTRIN AND CELLULOSIC POLYMER FILM COATINGS

This is a continuation of application Ser. No. 07/504,677 filed on Apr. 4, 1990 now abandoned.

BACKGROUND OF THE INVENTION

1. Field of the Invention

This invention is in the field of aqueous film coating of pharmaceutical, food, confectionery, and agricultural products, and is specifically concerned with providing coatings from a combination of maltodextrin and cellulosic polymers for coating such things as pharmaceutical tablets, pieces of candy, cereals, and agricultural seeds.

2. Description of the Prior Art

Cellulose polymers such as hydroxypropyl methylcellulose (HPMC) have long been recognized in the art as being suitable for aqueous film coating of pharmaceutical tablets and the like. To those skilled in the art, it is well known that as the molecular weight of the polymer is increased, the tensile strength of the film increases. This is also true for polymer blends whereby a high molecular weight polymer is added to a lower molecular weight polymer producing a substantially stronger film. Rowe, "Some Fundamental Properties of Polymeric Materials and Their Application in Film Coating Formulations", INT. J. PHARM TECH & PROD MFR., (3) Page 5, 1982, states that adding high molecular weight components to a composition of high and low molecular weight grades of a polymer can increase the effective tensile strength of that polymer. Rowe also states on page 3 of the same article that "the data presented almost exclusively pertains to the cellulose derivatives but the trends reported are likely to be the same for all polymers used in film coating."

Although an increase in molecular weight of a polymer blend is expected to increase the tensile strength of the coating, such an increase in molecular weight of the polymer blend decreases the clarity of the coating, and this is a drawback when it is desired to coat a substrate with a clear coating. Accordingly, a trade off has to be made between high tensile strength and high clarity. That is, to reduce cloudiness in a coating, the molecular weight of the polymer blend may be reduced, but this reduction in the molecular weight of the polymer blend would be expected to reduce the tensile strength of the coating.

Maltodextrins, which possess very low average molecular weights, would not be expected to enhance the strength of a film when blended with a polymer of higher molecular weight.

Also, when maltodextrins are combined with a single cellulosic polymer of higher molecular weight, the lower the molecular weight grade of maltodextrin used, the more the tensile strength of the film would be expected to decrease. We have found that, surprisingly, the opposite occurs.

SUMMARY OF THE INVENTION

An aqueous coating suspension comprises an effective amount of a combination of maltodextrin and a cellulosic polymer or polymers, and plasticizer mixed into water to form an aqueous suspension which may be applied to the substrates to be coated, as by spraying. In some cases, a secondary film former, a detackifier, and/or a flow aid are added to the mix. Optionally, a colorant may be added to the aqueous coating suspension before the coating step.

The film former of the coating is a mixture of maltodextrin and a cellulosic polymer film former, preferably methylcellulose, hydroxypropyl cellulose (HPC), hydroxypropyl methylcellulose (HPMC), hydroxyethyl cellulose, or carboxy methylcellulose.

The plasticizer may be polyethylene glycol, triacetin, propylene glycol, acetyltriethyl citrate, triethyl citrate, or glycerin.

The colorants may be FD & C lakes, D & C lakes, titanium dioxide or dyes approved for ingestion by the U.S. Federal Drug Administration. Examples of such pigments are listed in Colorcon U.S. Pat. No. 4,543,370 issued Sep. 24, 1985, which is incorporated herein by reference.

The detackifier may be lecithin or powdered stearic acid.

The secondary film former may be sodium alginate, propylene glycol alginate, or polyvinylpyrrolidone.

The flow aid may be silicates, such as talc, fumed silicas, or bentonite, or lubricating aids such as edible hydrogenated vegetable oils (stearines), or hydrogenated vegetable oils and waxes.

The quantity of maltodextrin is within the range of 5% to 78.5% by weight of the non-water ingredients of the aqueous coating suspension, and preferably is within the range of 20% to 50% by weight of the non-water ingredients of the aqueous coating suspension.

The quantity of the cellulosic polymer(s) is within the range of 4% to 90% by weight of the non-water ingredients of the aqueous coating suspension, and preferably is within the range of 20% to 70% by weight of the non-water ingredients of the aqueous coating suspension.

Preferably, the ratio by weight of maltodextrin to the cellulosic polymer(s) is 3 to 7 (3:7). That is, of just the film former in the dry formula, preferably 30% of the film former by weight is maltodextrin and 70% of the film former by weight is a cellulosic polymer or a combination of cellulosic polymers. However, a good coating still is obtained with the percentage of the maltodextrin in the film former being in the range of 5% to 95% by weight and the percentage of the cellulosic polymer or the combination of cellulosic polymers in the film former being in the range of 5% to 95% by weight.

The range for the plasticizer is 2.5% to 20% by weight of the non-water ingredients of the aqueous coating suspension, and the preferred range for the plasticizer is 5% to 10% by weight of the non-water ingredients of the aqueous coating suspension.

The ranges and preferred ranges for the remaining ingredients are as follows: secondary film former 0% to 15% with a preferred range of 0% to 10%; detackifier 0% to 15%, with a preferred range of 0% to 10%; flow aid 0% to 20%, with a preferred range of 0% to 10%; and a colorant 0% to 30%, with a preferred range of 0% to 20%. These ranges are all by weight of the non-water ingredients of the aqueous coating suspension.

Maltodextrin is available in varying levels of molecular weight as is hydroxypropyl methylcellulose. Dow ranks its Methocel hydroxypropyl methylcellulose products, HPMC E-3, HPMC E-6, HPMC E-15, HPMC E-50, etc,. in order of the increasing molecular weight, unlike Staley which ranks its maltodextrins, Star-Dri 1, Star-Dri 5, Star-Dri 10, Star-Dri 15, in order of decreasing molecular weight, with Star-Dri 1 possessing the highest molecular weight and Star-Dri 15 the lowest molecular weight. Gel permeation chromatography (GPC) analysis of average molecular weights of Dow's Methocel number series and Staley's maltodextrins (Star-Dri) are as follows:

| GRADE OF POLYMERS | LOT NO. | AVERAGE MOLECULAR WEIGHT |
|---|---|---|
| Methocel HPMC E-3 (Dow) | LC11126 | 26,247 |
| Methocel HPMC E-6 (Dow) | LC10738 | 73,476 |
| Methocel HPMC E-15 (Dow) | LC10236 | 131,393 |
| Methocel HPMC E-50 (Dow) | LC10679 | 174,971 |
| Maltodextrin Star-Dri 1 (Staley) | LC10837 | 56,955 |
| Maltodextrin Star-Dri 5 (Staley) | SS0641HA | 26,803 |
| Maltodextrin Star-Dri 10 (Staley) | SS1738GA | 7,692 |
| Maltodextrin Star-Dri 15 (Staley) | LC09452 | 1,470 |

Conditions:
TSK 3000, polyethylene oxide stds, 0.01M NaCl aqueous mobile phase

BRIEF DESCRIPTION OF THE DRAWINGS

FIG. 1 is a graph of tensile strength of hydroxypropyl methylcellulose films having 70% w/w of Methocel E-6 hydroxypropyl methylcellulose and 30% w/w of another hydroxypropyl methylcellulose versus the molecular weight of the 30% w/w hydroxypropyl methylcellulose;

FIG. 2 is a graph of modulus of elasticity of hydroxypropyl methylcellulose films having 70% w/w of Methocel E-6 hydroxypropyl methylcellulose and 30% w/w of another hydroxypropyl methylcellulose versus the molecular weight of the 30% w/w hydroxypropyl methycellulose;

FIG. 3 is a graph of tensile strength of films having 70% w/w of Methocel E-6 hydroxypropyl methylcellulose and 30% w/w of maltodextrin polymers versus the molecular weight of the 30% w/w maltodextrin polymers; and FIG. 4 is a graph of modulus of elasticity of films having 70% w/w of Methocel E-6 hydroxypropyl methylcellulose and 30% w/w of maltodextrin polymers versus the molecular weight of the 30% w/w maltodextrin polymers.

DETAILED DESCRIPTION

In tests, a number of HPMC coating films were made. Each such film included a polymer blend of 70% Methocel E-6 hydroxypropyl methylcellulose and 30% of another hydroxypropyl methylcellulose added thereto. The molecular weight of the added hydroxypropyl methylcellulose was different for each test. The HPMC coating films were prepared by dissolving each polymer combination in water, spreading the resultant solutions on glass plates, and allowing the films to dry. The dried films were then evaluated by tensile stress analysis using a JJ tensile tester.

As shown in FIGS. 1 and 2, as expected, the tensile strength and modulus of elasticity increased as the molecular weight of the additive hydroxypropyl methycellulose increased.

The test data illustrated in FIG. 1 is given below in Table 1, and the test data illustrated in FIG. 2 is given below in Table 2.

TABLE 1

| TENSILE STRENGTH (MPa) | v/s | MOLECULAR WEIGHT OF HPMC ADDED (×10³) |
|---|---|---|
| 50.6 (70% HPMC E-6/30% HPMC E-3) | | 26.25 (HPMC E-3) |
| 59.0 (100% HPMC E-6) | | 73.45 (HPMC E-6) |
| 62.1 (70% HPMC E-6/30% HPMC E-15) | | 131.39 (HPMC E-15) |
| 66.0 (70% HPMC E-6/30% HPMC E-50) | | 174.97 (HPMC E-50) |

TABLE 2

| MODULUS OF ELASTICITY (GPa) | v/s | MOLECULAR WEIGHT OF HPMC ADDED (×10³) |
|---|---|---|
| 2.550 (70% HPMC E-6/ 30% HPMC E-3) | | 26.25 (HPMC E-3) |
| 2.930 (100% HPMC E-6) | | 73.45 (HPMC E-6) |
| 2.920 (70% HPMC E-6/ 30% HPMC E-15) | | 131.39 (HPMC E-15) |
| 3.010 (70% HPMC E-6/ 30% HPMC E-50) | | 174.97 (HPMC E-50) |

HPMC and Maltodextrin

A number of coating films having a blended mixture of HPMC and maltodextrin also were made. Each such film included a polymer blend of 70% Methocel E-6 hydroxypropyl methylcellulose to which 30% maltodextrin was added. The molecular weight of the additive maltodextrin was different for each test. The coating films having a combination of HPMC and maltodextrin were prepared by dissolving each polymer combination in water, spreading the resultant solutions on glass plates, and allowing the films to dry. The dried films were then evaluated by tensile stress analysis using JJ tensile tester.

As shown in FIGS. 3 and 4, unexpectedly, the tensile strength and modulus of elasticity decreased as the molecular weight of the additive maltodextrin increased.

The test data illustrated in FIG. 3 is given below in Table 3, and the test data illustrated in FIG. 4 is given below in Table 4.

TABLE 3

| TENSILE STRENGTH (MPa) | v/s | MOLECULAR WEIGHT OF MALTODEXTRIN ADDED (×10³) |
|---|---|---|
| 33.3 (70% HPMC E-6/30% STAR-DRI 1) | | 56.950 (STAR-DRI 1) |
| 41.2 (70% HPMC E-6/30% STAR-DRI 5) | | 26.800 (STAR-DRI 5) |
| 44.0 (70% HPMC E-6/30% STAR-DRI 10) | | 7.690 (STAR-DRI 10) |
| 49.0 (70% HPMC E-6/30% STAR-DRI 15) | | 2.970 (STAR-DRI 15) |

TABLE 4

| MODULUS OF ELASTICITY (GPa) | v/s | MOLECULAR WEIGHT OF MALTODEXTRIN ADDED (×10³) |
|---|---|---|
| 1.894 (70% HPMC E-6/30% STAR-DRI 1) | | 56.950 (STAR-DRI 1) |
| 2.464 (70% HPMC E-6/30% STAR-DRI 5) | | 26.800 (STAR-DRI 5) |
| 2.756 (70% HPMC E-6/30% | | 7.690 (STAR-DRI 10) |

TABLE 4-continued

| MODULUS OF ELASTICITY (GPa) | v/s | MOLECULAR WEIGHT OF MALTODEXTRIN ADDED (×10³) |
|---|---|---|
| STAR-DRI 10) 3.304 (70% HPMC E-6/30% STAR-DRI 15) | | 2.970 (STAR-DRI 15) |

Accordingly, adding a lower molecular weight maltodextrin, rather than a higher molecular weight maltodextrin, to HPMC to form a polymer blend of HPMC and maltodextrin, produces a stronger coating. This is totally unexpected. Also, the coating was less cloudy.

These data show that while the addition of HPMC of increasing molecular weight to Methocel E-6 hydroxypropyl methycellulose produces expected results, namely, an INCREASE in tensile strength and modulus of elasticity, the addition of maltodextrin of increasing molecular weight produced exactly the opposite effect, namely, a DECREASE in tensile strength and modulus of elasticity. The results obtained with maltodextrin are totally unexpected. Similar trends are obtained when maltodextrins are added to other grades of cellulose ether polymers.

Consequently, a low molecular weight maltodextrin combined with a cellulosic polymer may be used to obtain a good coating film, and little or no trade off has to be made between clarity of the film and tensile strength of the film.

Further, since adding maltodextrin to cellulosic polymers decreases film strength, regardless of the anomaly of its behavior at varying molecular weight levels, maltodextrin would still be expected to produce film coatings that are entirely unsuitable to meet most modern film coating performance requirements. But, we have found that maltodextrin, in combination with cellulosic polymers of varying molecular weights, exhibits excellent adhesive qualities, enhanced gloss characteristics and reduced incidence of cloudiness (known as frost), often better than the film properties of HPMC and other cellulosic polymers alone.

Further, combinations of maltodextrin and cellulosic polymer may be formulated into dry, edible film coating compositions, shipped to the user dry, and then mixed easily into water to form aqueous coating solutions or suspensions.

The following examples of the invention all disclose formulations which may be mixed into water to form an aqueous coating solution or suspension effective to coat pharmaceutical tablets, food and confectionery pieces, and agricultural seeds. Seeds are advantageously coated to meet various needs, such as color coding for identification purposes, adhesion of various additives (e.g., pest control agents and inocula), prevention of handling damage and to allow the use of mechanical planting equipment.

The coated forms include medicinal tablets, vitamin tablets, aspirin tablets, capsules, chewing gum balls, candy pieces, breakfast cereals, and agricultural seeds.

EXAMPLES

The following examples illustrate the invention. All units and percentages used herein are by weight.

EXAMPLE 1

A clear coating suspension is made for coating aspirin tablets with a thin coating making them easy to swallow and eliminating the characteristic aspirin taste. The following ingredients are mixed into water to form an aqueous coating solution.

| | percent | Gms |
|---|---|---|
| Maltodextrin (Star-Dri 10) | 27.0 | 27.0 |
| HPMC (Methocel HPMC E-6) | 45.5 | 45.5 |
| HPMC (Methocel HPMC E-3) | 14.0 | 14.0 |
| HPMC (Methocel HPMC E-50) | 3.5 | 3.5 |
| PEG 400 | 10.0 | 10.0 |
| | 100.0 | 100.0 |

Star-Dri 10 maltodextrin is supplied by Staley Company; Methocel HPMC E-6, E-3, and E-50 are supplied by Dow Chemical Company. The combination of HPMC and maltodextrin is the film former. The PEG 400 is polyethylene glycol 400 (Union Carbide), and it is used in the formula as a plasticizer.

The coating suspension is prepared by blending all dry ingredients in a blender for five minutes, adding PEG 400 and blending for an additional five minutes. Then, 100 grams of the above mixture is stirred into 900 milliliters of water to make an aqueous coating suspension.

Ten kilograms of embossed aspirin cores are placed in a 24" Accela-Cota coating pan with four anti-skid bars. The aqueous coating suspension is sprayed onto the aspirin tablets using two #605 Binks air guns, 66 fluid nozzles, 66 SH air caps and a #7565-10 Masterflex peristaltic pump with two #7015 pump heads. During the coating procedure, the atomizing air is 35 psi, the inlet air is 75° centigrade, the outlet air is 45° centigrade, the pan speed is 8 rpm, the coating liquid feed rate is 65 grams/minute, and the coating time is 15 minutes. The procedure produces very smooth, glossy, thinly coated aspirin cores that are non-tacky and easy to swallow. Further, the characteristic aspirin taste is not observed when a coated core is swallowed.

EXAMPLE 2

The coating solution is made as in Example 1 and vitamin tablets are spray coated as in Example 1.

EXAMPLE 3

The coating mixture is made as in Example 1 having the following formula:

| | percent | Gms |
|---|---|---|
| Maltodextrin (Star-Dri 5) | 27.0 | 27.0 |
| HPMC (Methocel HPMC E-6) | 45.5 | 45.5 |
| HPMC (Methocel HPMC E-3) | 14.0 | 14.0 |
| HPMC (Methocel HPMC E-50) | 3.5 | 3.5 |
| PEG 400 | 10.0 | 10.0 |
| | 100.0 | 100.0 |

The coating solution is made as in Example 1 and a 10 kilogram charge of mixed medicinal tablets, including acetaminophen, aspirin, ibuprofen, and vitamins is spray coated as in Example 1.

EXAMPLE 4

A coating mixture is made as in Example 1 having the following formula:

| | percent | Gms |
|---|---|---|
| Maltodextrin (Star-Dri 15) | 27.0 | 27.0 |
| HPMC (Methocel HPMC E-6 | 45.5 | 45.5 |
| HPMC (Methocel HPMC E-3) | 14.0 | 14.0 |

|  | percent | Gms |
|---|---|---|
| HPMC (Methocel HPMC E-50) | 3.5 | 3.5 |
| PEG 400 | 10.0 | 10.0 |
|  | 100.0 | 100.0 |

The coating solution is made as in Example 1 and a 10 kilogram charge of mixed medicinal tablets as described in Example 3 is spray coated as in Example 1.

EXAMPLE 5

It is often desirable to overcoat a pigmented cellulosic film polymer coating with a clear thin coating layer that imparts gloss and enables the tablet to be easily swallowed.

Acetaminophen caplets are spray coated in a 24" Accela-Cota, equipped as in Example 1, with an OPADRY® coating suspension made in accordance with the disclosure in Colorcon U.S. Pat. No. 4,543,370, issued Sep. 24, 1985, which is incorporated herein by reference.

The caplets are then overcoated with a coating mixture as in Example 1. The coating solution is obtained by stirring 50 grams of the dry mix of Example 1 into 450 milliliters of water. The spray coating parameters are inlet air 80° centigrade, outlet air 45° centigrade, atomizing air 35 psi, pan speed 8 rpm, the solution feed rate is 62 grams/minute, and the coating time for the overcoat alone is 8 minutes. The coated caplets are non-tacky, very smooth and shiny.

EXAMPLE 6

It is often desirable to incorporate a colorant into the aforementioned formulae. The coating mixture is made as in Example 1, having the following dry formula:

|  | percent | Gms |
|---|---|---|
| Maltodextrin (Star-Dri 10) | 30.00 | 90.00 |
| HPMC (Methocel HPMC E-6) | 28.89 | 86.67 |
| HPMC (Methocel HPMC E-3) | 8.89 | 26.67 |
| HPMC (Methocel HPMC E-50) | 2.22 | 6.66 |
| PEG 400 | 10.00 | 30.00 |
| Titanium Dioxide | 16.00 | 48.00 |
| FD & C Yellow #6 HT Lake | 4.00 | 12.00 |
|  | 100.00 | 300.00 |

The titanium dioxide is an opacifier and the FD & C Yellow #6 HT lake is an aluminum lake manufactured by Colorcon, West Point, Pa., and gives the coating an orange color.

The coating suspension is made by mixing 300 grams of dry formula into 1700 milliliters of water and then spraying it onto 10 kilograms of mixed medicinal tablets, including acetaminophen, various aspirin tablets, ibuprofen, and vitamin tablets in a 24" Accela-Cota as in Example 1. The spray coating parameters are inlet air at 75° centigrade, outlet air at 45° centigrade, atomizing air at 3 bar, pan speed at 12 rpm, and feed rate at 65 grams/minute. The total coating time is 30 minutes. The tablets are fully coated and smooth, with good logo definition.

EXAMPLE 7

The coating mixture is made as in Example 1, having the following formula:

|  | percent | Gms |
|---|---|---|
| Maltodextrin (Star-Dri 10) | 21.00 | 63.00 |
| HPMC (Methocel HPMC E-6) | 35.39 | 106.17 |
| HPMC (Methocel HPMC E-3) | 10.89 | 32.67 |
| HPMC (Methocel HPMC E-50) | 2.72 | 8.16 |
| PEG 400 | 10.00 | 30.00 |
| Titanium Dioxide | 16.00 | 48.00 |
| FD & C Yellow #6 HT Lake | 4.00 | 12.00 |
|  | 100.00 | 300.00 |

The coating suspension is prepared as in Example 1 and the medicinal tablets are spray coated as in Example 6.

EXAMPLE 8

A breakfast cereal is coated with a colored aqueous coating suspension of the following formula mixed as in Example 1:

|  | percent | Gms |
|---|---|---|
| Maltodextrin (Star-Dri 5) | 30.00 | 3.75 |
| HPMC (Methocel HPMC E-6) | 28.89 | 3.61 |
| HPMC (Methocel HPMC E-3) | 8.89 | 1.11 |
| HPMC (Methocel HPMC E-50) | 2.22 | 0.28 |
| PEG 400 | 10.00 | 1.25 |
| Titanium Dioxide | 16.00 | 2.00 |
| FD & C Yellow #6 HT Lake | 4.00 | 0.50 |
|  | 100.00 | 12.50 |

The suspension is prepared as in Example 1. The form to be sprayed in this example is puffs of KIX breakfast cereal. The cereal puffs are sprayed in a fluidized bed coater, made by Aeromatic. The operator partly fills the bed coater cone with KIX cereal puffs, approximately 125–150 grams, starts the turbine to fluidize the puffs, and sprays them with the aqueous suspension of Example 8 having 7.5% solids. The inlet temperature is 60° centigrade; the outlet temperature is 30° centigrade; the atomizing air is 2 bar, and the solution feed rate is 10 grams per minute.

EXAMPLE 9

Pistachio nuts are coated using the following formula:

|  | percent | Gms |
|---|---|---|
| Maltodextrin (Star-Dri 1) | 30.14 | 3.014 |
| HPMC (Methocel HPMC E-6) | 30.14 | 3.014 |
| Kelcoloid S | 9.44 | 0.944 |
| PEG 400 | 9.45 | 0.945 |
| Titanium dioxide | 8.33 | 0.833 |
| FD & C Red #40 HT Lake | 9.72 | 0.972 |
| Stearic Acid | 2.78 | 0.278 |
|  | 100.00 | 10.000 |

The powder coating is mixed into water as in Example 1 to make an aqueous coating suspension of 15% solids. A fluidized bed coating chamber as in Example 8 is filled with a 500 gram charge of unshelled pistachio nuts. The nuts are then sprayed with the coating suspension and the coating parameters are inlet temperature 60° centigrade, outlet temperature 40° centigrade, atomizing air 3 bar, and feed rate 10 grams/minute.

Kelcoloid S is propylene glycol alginate (Kelco Division of Merck & Co.) and is used as a secondary film former. Stearic acid (Witco Chemical Corporation) is used as a detackifier in the formula. FD & C Red #40 HT Lake is an aluminum lake manufactured by Colorcon, West Point, Pa., and gives the coating a red color.

EXAMPLE 10

Chocolate pieces are coated using the formula of Example 6. Ten kilograms of chocolate pieces are placed in a 24" Accela-Cota coating pan and rotated at 12 rpm. The pieces are then subcoated to provide an even surface to which the colored coating will be applied. The subcoat is a polydextrose based aqueous coating suspension made in accordance with the disclosure in Colorcon U.S. Pat. No. 4,802,924, issued Feb. 17, 1989, which is incorporated herein by reference. The subcoated chocolate pieces are then spray coated with the formula of Example 6 at 22.5% solids. The spray coating parameters are inlet air 33° centigrade, outlet air 23° centigrade, atomizing air 45 psi, feed rate 24 grams/minute, and the coating time is 50 minutes.

EXAMPLE 11

To apply a colored coating composition to agricultural seeds, the following ingredients are mixed into water as in Example 1 to form an aqueous coating suspension of 20% solids:

|  | percent | Gms |
| --- | --- | --- |
| Maltodextrin (Star-Dri 1) | 36.0 | 63.000 |
| HPMC (Methocel HPMC E-6) | 15.5 | 27.125 |
| HPMC (Methocel HPMC E-3) | 15.5 | 27.125 |
| HPMC (Methocel HPMC E-50) | 5.0 | 8.750 |
| Triacetin | 8.0 | 14.000 |
| Titanium Dioxide | 12.0 | 21.000 |
| FD & C Blue #1 HT Lake | 8.0 | 14.000 |
|  | 100.0 | 175.000 |

Three and a half kilograms of squash seeds (Asgrow Seed Company) are placed in an 18" conventional pan with 6 anti-slide baffles. The pan is rotated at 22 rpm, and the aqueous coating suspension is sprayed onto the seeds by a #460 Binks air gun, using a #7565-10 Masterflex peristaltic pump, with a 7016 pump head. During the coating procedure, the inlet air is 50° centigrade, outlet air is 28° centigrade, atomizing air is 35 psi, feed rate is 16 grams/minute and the coating time is 55 minutes. The coating adheres well to the seed surface and the seeds are smooth and non-tacky.

The triacetin is glycerol tiracetate and is used as a plasticizer in the formula, and the FD & C Blue #1 HT lake is an aluminum lake manufactured by Colorcon, West Point, Pa., and gives the coating a blue color.

EXAMPLE 12

Functional additives such as fungicides and the like are mixed into the dry mixture formula of Example 11, and this dry mixture is mixed into water as in Example 11 to form a coating suspension. The aqueous coating is then sprayed onto seeds as in Example 11.

Alternatively, the additives may be stirred directly into the coating suspension, rather than dry mixing it into the dry coating mixture.

EXAMPLE 13

A coating mixture is made as in Example 1 having the following formula:

|  | percent | Gms |
| --- | --- | --- |
| Maltodextrin (Star-Dri 1) | 31.0 | 17.36 |
| HPMC (Methocel HPMC E-6) | 13.0 | 7.28 |
| HPMC (Methocel HPMC E-3) | 13.0 | 7.28 |

-continued

|  | percent | Gms |
| --- | --- | --- |
| HPMC (Methocel HPMC E-50) | 5.0 | 2.80 |
| Triacetin | 8.0 | 4.48 |
| Talc | 10.0 | 5.60 |
| Titanium Dioxide | 12.0 | 6.72 |
| FD & C Blue #1 HT | 8.0 | 4.48 |
|  | 100.0 | 56.00 |

A coating suspension is prepared as in Example 1. Then 800 grams of onion seeds (Petoseed Seed Company) are sprayed in an Aeromatic Strea-1 fluidized bed coater with a 1.1 mm fluid nozzle. The coating parameters are inlet temperature 50° centigrade, outlet temperature 28° centigrade, atomizing air 2 bar, feed rate 8 grams/minute and the coating time is 35 minutes. A weight gain of approximately 7.0% is applied, and the seeds are smooth and non-tacky as in Example 11.

Talc is magnesium silicate and is used in the formula as a flow aid.

Other examples of coatings that illustrate the invention are as follows. They are sprayed onto agricultural seeds such as seeds for cucumbers, beets, carrots, and radishes. The dry coating mixtures and the liquid coating suspensions or solutions are made as in Example 1, and the seeds are spray coated as in Example 13.

EXAMPLE 14

|  | percent | Gms |
| --- | --- | --- |
| Maltodextrin (Star-Dri 10) | 36.0 | 11.52 |
| HPMC (Methocel HPMC E-6) | 15.5 | 4.96 |
| HPMC (Methocel HPMC E-3) | 15.5 | 4.96 |
| HPMC (Methocel HPMC E-50) | 5.0 | 1.60 |
| Triacetin | 8.0 | 2.56 |
| Titanium Dioxide | 12.0 | 3.84 |
| FD & C Blue #1 HT Lake | 8.0 | 2.56 |
|  | 100.00 | 32.00 |

A 4% weight gain is obtained by spraying.

EXAMPLE 15

|  | percent | Gms |
| --- | --- | --- |
| Maltodextrin (Star-Dri 1) | 33.0 | 9.90 |
| HPMC (Methocel HPMC E-6) | 16.5 | 4.95 |
| HPMC (Methocel HPMC E-3) | 16.5 | 4.95 |
| Kelgin LV | 4.0 | 1.20 |
| Alcolec F-100 | 2.5 | 0.75 |
| Triacetin | 3.0 | 0.90 |
| Titanium Dioxide | 12.5 | 3.75 |
| FD & C Red #40 HT Lake | 12.0 | 3.60 |
|  | 100.0 | 30.00 |

Kelgin LV is sodium alginate (Kelco Division of Merck & Company) and is used as a secondary film former. Alcolec F-100 is lecithin (American Lecithin Company) and is used as a detackifier in the formula.

A 3% weight gain is obtained by spraying.

EXAMPLE 16

|  | percent | Gms |
|---|---|---|
| Maltodextrin (Star-Dri 1) | 34.0 | 10.20 |
| HPMC (Methocel HPMC E-6) | 14.5 | 4.35 |
| HPMC (Methocel HPMC E-3) | 14.5 | 4.35 |
| HPMC (Methocel HPMC E-50) | 5.0 | 1.50 |
| Talc | 4.0 | 1.20 |
| Triacetin | 8.0 | 2.40 |
| Titanium Dioxide | 4.0 | 1.20 |
| D & C Yellow #10 HT Lake | 16.0 | 4.80 |
|  | 100.0 | 30.00 |

D & C Yellow #10 HT Lake is an aluminum lake manufactured by Colorcon, West Point, Pa. and gives the coating a yellow color.

A 3% weight gain is obtained by spraying.

EXAMPLE 17

|  | percent | Gms |
|---|---|---|
| Maltodextrin (Star-Dri 1) | 36.0 | 20.16 |
| HPMC (Methocel HPMC E-6) | 15.5 | 8.68 |
| HPMC (Methocel HPMC E-3) | 15.5 | 8.68 |
| HPMC (Methocel HPMC E-50) | 5.0 | 2.80 |
| Triacetin | 8.0 | 4.48 |
| Bentonite | 6.0 | 3.36 |
| Titanium Dioxide | 6.0 | 3.36 |
| FD & C Blue #1 HT Lake | 8.0 | 4.48 |
|  | 100.0 | 56.00 |

Bentonite is an aluminum silicate (American Colloid Company) and is used in the formula as a flow aid.

A 7% weight gain is obtained by spraying.

EXAMPLE 18

A clear version of the preceding formulations is used on agricultural seeds as a carrier by which to apply performance additives such as fungicides and the like to the surface of the seed. A clear coating mixture is made as in Example 12 having the following formula:

|  | percent | Gms |
|---|---|---|
| Maltodextrin (Star-Dri 1) | 43.50 | 24.36 |
| HPMC (Methocel HPMC E-6) | 21.75 | 12.18 |
| HPMC (Methocel HPMC E-3) | 21.75 | 12.18 |
| HPMC (Methocel HPMC E-50) | 5.00 | 2.80 |
| Triacetin | 8.00 | 4.48 |
|  | 100.00 | 56.00 |

The coating solution is prepared as in Example 1, except, after the dry coating mix is stirred into the water, the additives are mixed into the water. The agricultural seeds are spray coated as in Example 11.

EXAMPLE 19

Another clear aqueous coating formulation for agricultural seeds is as follows:

|  | percent | Gms |
|---|---|---|
| Maltodextrin (Star-Dri 1) | 33.50 | 18.76 |
| HPMC (Methocel HPMC E-6) | 16.75 | 9.38 |
| HPMC (Methocel HPMC E-3) | 16.75 | 9.38 |
| HPMC (Methocel HPMC E-50) | 5.00 | 2.80 |
| Triacetin | 8.00 | 4.48 |
| Talc | 20.00 | 11.20 |
|  | 100.00 | 56.00 |

A coating suspension is prepared as in Example 1, and is spray coated onto agricultural seeds as in Example 11.

EXAMPLE 20

Another clear aqueous formulation for agricultural seeds is as follows:

|  | percent | Gms |
|---|---|---|
| Maltodextrin (Star-Dri 1) | 38.80 | 12.42 |
| HPMC (Methocel HPMC E-6) | 19.40 | 6.20 |
| HPMC (Methocel HPMC E-3) | 19.40 | 6.20 |
| HPMC (Methocel HPMC E-50) | 4.40 | 1.41 |
| PVP | 10.00 | 3.21 |
| Triacetin | 8.00 | 2.56 |
|  | 100.00 | 32.00 |

A coating solution is prepared as in Example 1, and is spray coated onto agricultural seeds as in Example 11.

PVP is polyvinylpyrrolidone and is used in the formula as a secondary film former.

EXAMPLE 21

Another clear aqueous coating formulation for agricultural seeds is as follows:

|  | percent | Gms |
|---|---|---|
| Maltodextrin (Star-Dri 1) | 41.10 | 13.15 |
| HPMC (Methocel HPMC E-6) | 20.60 | 6.60 |
| HPMC (Methocel HPMC E-3) | 20.60 | 6.60 |
| HPMC (Methocel HPMC E-50) | 4.70 | 1.50 |
| Triacetin | 8.00 | 2.55 |
| Stearotex-C | 5.00 | 1.60 |
|  | 100.00 | 32.00 |

A coating solution is prepared as in Example 1, and is spray coated onto agricultural seeds as in Example 11.

Stearotex-C is a lubricating aid (Capital City Products, Co.) and is used in the formula as a flow-aid.

EXAMPLE 22

A clear aqueous coating mixture is made as in Example 1 having the following formula:

|  | percent | Gms |
|---|---|---|
| Maltodextrin (Star-Dri 10) | 76.0 | 3.80 |
| HPMC (Methocel HPMC E-50) | 4.0 | 0.20 |
| PEG 3350 | 20.0 | 1.00 |
|  | 100.0 | 5.00 |

A 5% solids coating solution is made as in Example 1 and a 500 gm charge of ⅜-inch concave placebos is spray coated in an Aeromatic Strea-1 fluidized bed coater with a 1.1 mm fluid nozzle. The spray coating parameters are inlet temperature 60° centigrade, outlet temperature 32° centigrade, atomizing air 2 bar, and fluid delivery rate 10 gms/min. A weight gain of approximately 1.0% is obtained.

PEG 3350 is polyethylene glycol (Union Carbide) and is used as a plasticizer in the formula.

Other formulations of clear coating mixtures are as follows. These dry mixtures are made into coating solutions and spray-coated onto ⅜-inch concave placebos as in Example 22 or spray coated onto medicinal tablets as in Example 1, and the coatings on the placebos and tablets are smooth and non-tacky.

EXAMPLE 23

|  | percent | Gms |
|---|---|---|
| HPMC (Methocel HPMC E-3) | 67.0 | 3.35 |
| HPMC (Methocel HPMC E-6) | 16.0 | 0.80 |
| Klucel EF | 7.0 | 0.35 |
| Maltodextrin (Star-Dri 1) | 5.0 | 0.25 |
| Propylene Glycol | 5.0 | 0.25 |
|  | 100.0 | 5.00 |

Klucel EF is hydroxypropyl cellulose (Hercules Co.) and is used in the formula as the primary film former in combination with the maltodextrin and HPMC's. Propylene glycol (Van Waters & Rogers) is used in the formula as a plasticizer.

EXAMPLE 24

|  | percent | Gms |
|---|---|---|
| Maltodextrin (LoDex 5) | 27.0 | 1.35 |
| HPMC (Methocel E-6) | 45.5 | 2.28 |
| CMC-7LF | 14.0 | 0.70 |
| HPMC (Methocel E-50) | 3.5 | 0.17 |
| Glycerin | 8.0 | 0.40 |
| Cabosil EH5 | 2.0 | 0.10 |
|  | 100.0 | 5.00 |

LoDex 5 is maltodextrin from Amaizo Co. CMC-7LF is carboxy methylcellulose from Aqualon and is used in combination with the maltodextrin and HPMC's as the primary film former of the formula. Glycerin (Van Waters & Rogers) is used as a plasticizer in the formula. Cabosil EH5 is colloidal silicon dioxide (fumed silica) (Cabot Co.) and is used as a flow-aid.

EXAMPLE 25

|  | percent | Gms |
|---|---|---|
| Maltodextrin (LoDex 5) | 27.0 | 1.35 |
| HPMC (Methocel E-6) | 45.5 | 2.28 |
| Methocel A-15LV | 14.0 | 0.70 |
| HPMC (Methocel E-50) | 3.5 | 0.17 |
| Citroflex A-2 | 8.0 | 0.40 |
| Cabosil EH5 | 2.0 | 0.10 |
|  | 100.0 | 5.00 |

Methocel A-15LV is Premium Grade Methylcellulose (Dow Chemical) and is used in combination with HPMC's and maltodextrin as the primary film former of the formula.

Citroflex A-2 is acetyl triethyl citrate (Pfizer Co.) and is used as a plasticizer.

EXAMPLE 26

|  | percent | Gms |
|---|---|---|
| Maltodextrin (Star-Dri 15) | 27.0 | 1.35 |
| Pharmacoat 603 | 45.5 | 2.28 |
| Natrosol 250 LNF | 14.0 | 0.70 |
| Metalose 60SH-50 | 3.5 | 0.17 |
| PEG 8000 | 10.0 | 0.50 |
|  | 100.0 | 5.00 |

Pharmacoat 603 and Metalose 60SH-50 are grades of hydroxypropyl methylcellulose (Shin-Etsu), and Natrosol 250 LNF is hydroxy ethylcellulose (Aqualon). All three polymers are used in combination with maltodextrin as the primary film former of the formula.

PEG 8000 is polyethylene glycol (Union Carbide) and is used as a plasticizer.

EXAMPLE 27

A colored aqueous coating suspension is made as in Example 1 having the following formula:

|  | percent | Gms |
|---|---|---|
| Maltodextrin (Star-Dri 1) | 30.14 | 4.52 |
| CMC-7LF | 30.14 | 4.52 |
| Kelcoloid S | 9.44 | 1.41 |
| Citroflex-2 | 9.45 | 1.42 |
| Titanium Dioxide | 8.33 | 1.25 |
| FD&C Red #40 HT Lake | 9.72 | 1.46 |
| Sterotex | 2.78 | 0.42 |
|  | 100.00 | 15.00 |

A 15% solids solution is prepared as in Example 1 and a 500 gm charge of ⅜-inch concave placebos is spray coated as in Example 22. The spray coating parameters are inlet temperature 60° centigrade, outlet temperature 40° centigrade, atomizing air 2.5 bar, fluid delivery rate 10 gm/min, and the approximate weight gain is 3.0%.

Citroflex-2 is triethyl citrate (Pfizer Co.) and is used in the formula as a plasticizer. Sterotex is a lubricating aid (Capital City Products, Co.) and is used in the formula as a flow-aid.

EXAMPLE 28

Into 850 milliliters of water, the following is added:

|  | percent | Gms |
|---|---|---|
| Maltodextrin (Star-Dri 10) | 27.00 | 40.50 |
| HPMC (Methocel HPMC E-6) | 45.50 | 68.25 |
| HPMC (Methocel HPMC E-3) | 14.00 | 21.00 |
| HPMC (Methocel HPMC E-50) | 3.50 | 5.25 |
| PEG 400 | 10.00 | 15.00 |
|  | 100.00 | 150.00 |

The coating suspension is then spray dried in a Lab Plant spray drier, model SD-04 (The Virtis Company Inc.). The spray drier parameters are as follows:

| inlet temperature | 200°–225° centigrade |
|---|---|
| outlet temperature | 110°–115° centigrade |
| feed rate of material | 0.5–0.75 liters/hour |
| blower setting | 94–95 |
| compressor setting | full (+) |

| | |
|---|---|
| spray nozzle | 1 mm |

The drying time of the suspension is 45 minutes, and the result is a fluffy, dry, edible coating composition. One hundred grams of the coating composition is stirred into 900 milliliters of water to make an aqueous coating solution, which is sprayed onto aspirin tablets as in Example 1.

EXAMPLE 29

Into 850 milliliters of water, the following is added:

| | percent | Gms |
|---|---|---|
| Maltodextrin (Star-Dri 10) | 30.00 | 45.00 |
| HPMC (Methocel HPMC E-6) | 28.89 | 43.34 |
| HPMC (Methocel HPMC E-3) | 8.89 | 13.34 |
| HPMC (Methocel HPMC E-50) | 2.22 | 3.33 |
| PEG 400 | 10.00 | 15.00 |
| Titanium Dioxide | 16.00 | 24.00 |
| FD&C Yellow #6 HT Lake | 4.00 | 6.00 |
| | 100.00 | 150.00 |

The coating suspension is then spray dried in a Lab Plant spray drier. The drying parameters for the spray drier are as follows:

| | |
|---|---|
| inlet temperature | 180°–212° centigrade |
| outlet temperature | 121°–132° centigrade |
| feed rate of material | 13 grams/minute |
| blower setting | 94 |
| compressor setting | full (+) |
| spray nozzle | 1 mm |

The drying time of the pigmented suspension is 75 minutes and the result is a dry, edible, pigmented coating composition. One hundred grams of the coating composition is stirred into 900 milliliters of water to make an aqueous coating suspension, which is sprayed onto aspirin tablets as in Example 1.

EXAMPLE 30

A pigmented aqueous coating mixture is made as in Example 1 having the following formula:

| | percent | Gms |
|---|---|---|
| Maltodextrin (Star-Dri 5) | 18.00 | 54.00 |
| HPMC (Methocel HPMC E-3) | 30.33 | 90.99 |
| HPMC (Methocel HPMC E-6) | 9.34 | 28.02 |
| HPMC (Methocel HPMC E-50) | 2.33 | 6.99 |
| PEG 8000 | 10.00 | 30.00 |
| Titanium Dioxide | 30.00 | 90.00 |
| | 100.00 | 300.00 |

An 18% solids coating suspension is made as in Example 1 and a 10 kilogram charge of mixed medicinal tablets as in Example 3 is spray coated as in Example 1. The spray coating parameters are inlet temperature 80° centigrade, outlet temperature 40° centigrade, fluid delivery rate 61 grams/minute, atomizing air 35 psi, pan speed 12 rpm. Approximately 3.0% weight gain is applied. The tablets are very smooth, non-tacky and elegantly coated.

EXAMPLE 31

A clear aqueous coating mixture is made as in Example 1 having the following formula:

| | percent | Gms |
|---|---|---|
| Maltodextrin (Star-Dri 15) | 78.5 | 3.925 |
| HPMC (Methocel HPMC E-50) | 4.0 | 0.200 |
| PEG 8000 | 2.5 | 0.125 |
| Stearic Acid | 15.0 | 0.750 |
| | 100.00 | 5.000 |

The coating solution is made as in Example 1 and a 500 gm charge of ⅜-inch concave placebos is spray coated as in Example 22.

A dry edible film composition for use in coating pharmaceutical tablets, food, confectionery forms and agricultural seeds with a protective film comprises a cellulosic polymer(s), maltodextrin and a plasticizer, and optionally, any or all of the following: secondary film former, detackifier, flow aid, and a colorant.

The dry edible film composition is prepared by blending together all the dry ingredients of the coating formula, and then blending the liquid plasticizer therein.

Alternatively, the dry edible film composition may be prepared by stirring the ingredients of the coating formulation one by one in a conventional manner into water to form a coating suspension. Then, the coating suspension may be spray dried to form a dry edible film composition that may be remixed into water when desired to form a coating suspension which is then sprayed onto the forms, cores, or substrates.

We claim:

1. A method of coating substrates from the group consisting of pharmaceutical tablets, food and confectionery forms, and agricultural seeds, with a protective film comprising the steps of mixing a film former, the film former including a film forming amount of cellulosic polymer and a film forming amount of maltodextrin, and a plasticizer into water to form an aqueous coating suspension, the cellulosic polymer being in a range of greater than 5% to about 90% by weight of the non-water ingredients of the aqueous coating suspension, the maltodextrin being in a range of about 5% to about 78.5% by weight of the non-water ingredients of the aqueous coating suspension, and the plasticizer being in a range of about 2.5% to about 20% by weight of the non-water ingredients of the aqueous coating suspension, applying an effective amount of said coating suspension onto said substrates to form a film coating of the film former on said substrates, and drying the film coating on said substrates.

2. The method of claim 1, including dispersing a detackifier into the aqueous coating suspension.

3. The method of claim 1, including dispersing a secondary film former into the aqueous coating suspension.

4. The method of claim 1, including dispersing a flow aid into the aqueous coating suspension.

5. The method of claim 1, including dispersing a colorant into the coating suspension before applying the coating suspension to the substrates.

6. The method of claim 1, wherein the plasticizer is selected from the group consisting of polyethylene glycol, triacetin, propylene glycol, acetyltriethyl citrate, triethyl citrate, and glycerin.

7. A method of making a dry edible film coating composition for use in coating pharmaceutical tablets, food and confectionery forms, and agricultural seeds, with a protective film, comprising the steps of mixing a film former, the film former including a film forming amount of cellulosic polymer and a film forming amount of maltodextrin, and a plasticizer into a solvent to form a coating dispersion, the cellulosic polymer being in a range of greater than 5% to about 90% by weight of non-solvent ingredients of the coating dispersion, the maltodextrin being in a range of about 5% to about 78.5% by weight of non-solvent ingredients of the coating dispersion, and the plasticizer being in a range of about 2.5% to about 20% by weight of non-solvent ingredients for the coating dispersion, evaporating the solvent in the coating dispersion to obtain the dry edible film coating composition, further including mixing a detackifier, a secondary film former, a flow aid, and a colorant into the solvent when forming the coating dispersion.

8. The method of claim 1, wherein the plasticizer is in a range of 5.0% to 10.0% by weight of the non-water ingredients of the aqueous coating suspension.

9. The method of claim 2, wherein the detackifier is selected from the group consisting of lecithin and stearic acid.

10. The method of claim 2, wherein the detackifier is in a range of 0% to 15% by weight of the non-water ingredients of the aqueous coating suspension.

11. The method of claim 2, wherein the detackifier is in a range of 0% to 10% by weight of the non-water ingredients of the aqueous coating suspension.

12. The method of claim 3, wherein the secondary film former is selected from the group consisting of sodium alginate, propylene glycol alginate, and polyvinylpyrrolidone.

13. The method of claim 3, wherein the secondary film former is in a range of 0% to 10% by weight of the non-water ingredients of the aqueous coating suspension.

14. The method of claim 3, wherein the secondary film former is in a range of 0% to 5% by weight of the non-water ingredients of the aqueous coating suspension.

15. The method of claim 4, wherein the flow aid is selected from the group consisting of talc, fumed silica, bentonite, edible hydrogenated vegetable oils and hydrogenated vegetable oil and waxes.

16. The method of claim 4, wherein the flow aid is in a range of 0% to 20% by weight of the non-water ingredients of the aqueous coating suspension.

17. The method of claim 4, wherein the flow aid is in a range of 0% to 10% by weight of the non-water ingredients of the aqueous coating suspension.

18. The method of claim 5, wherein said colorants are selected from the group consisting of FD & C lakes, D & C lakes, titanium dioxide and dyes.

19. The method of claim 5, wherein said colorants are in a range of 0% to 30% by weight of the non-water ingredients of the aqueous coating suspension.

20. The method of claim 5, wherein the colorants are in a range of 0% to 20% by weight of the non-water ingredients of the aqueous coating suspension.

21. The method of making a coating dispersion for coating substrates from the group consisting of pharmaceutical tablets, food and confectionery forms, and agricultural seeds, comprising the steps of mixing a film former, the film former including a film forming amount of cellulosic polymer and a film forming amount of maltodextrin, and a plasticizer into water to form an aqueous coating dispersion, the cellulosic polymer being in a range of greater than 5% to about 90% by weight of non-water ingredients of the coating dispersion, the maltodextrin being in a range of about 5% to about 78.5% by weight of non-water ingredients of the coating dispersion, and the plasticizer being in a range of about 2.5% to about 20% by weight of non-water ingredients of the coating dispersion, further including dispersing a detackifier, a secondary film former, a flow aid, and a colorant into the aqueous coating dispersion.

22. The method of claim 1, the maltodextrin being in a range of 20% to 50% by weight of the non-water ingredients of the aqueous coating suspension.

23. The method of claim 1, wherein the cellulosic polymer is selected from the group consisting of methylcellulose, hydroxypropyl cellulose, hydroxypropyl methylcellulose, hydroxyethyl cellulose, and carboxy methylcellulose.

24. An aqueous coating dispersion for coating substrates from the group consisting of pharmaceutical tablets, food and confectionery forms, and agricultural seeds, comprising a mixture of a film former, the film former including a film forming amount of cellulosic polymer and a film forming amount of maltodextrin, a plasticizer, and water, the cellulosic polymer being in a range of greater than 5% to about 90% by weight of the non-water ingredients of the aqueous coating suspension, the maltodextrin being in a range of about 5% to about 78.5% by weight of the non-water ingredients of the aqueous coating suspension, and the plasticizer being in a range of about 2.5% to about 20% by weight of the non-water ingredients of the aqueous coating suspension, further including a detackifier, a secondary film former, a flow aid, and a colorant.

25. The method of claim 1, wherein the cellulosic polymer is in a range of 30% to 70% by weight of the non-water ingredients of the aqueous coating suspension.

26. A coated substrate produced by the method of claim 1.

27. A coated substrate produced by the method of claim 2.

28. A coated substrate produced by the method of claim 3.

29. A coated substrate produced by the method of claim 4.

30. A coated substrate produced by the method of claim 5.

31. A method of coating substrates from the group consisting of pharmaceutical tablets, food and confectionery forms, and agricultural seeds, with a protective film comprising the steps of mixing a film former, the film former including a film forming amount of cellulosic polymer and a film forming amount of maltodextrin, a plasticizer, a detackifier, a secondary film former, a flow aid, and a colorant into water to form an aqueous coating suspension, the cellulosic polymer being in a range of about 30% to 70% by weight of the non-water ingredients of the aqueous coating suspension, the maltodextrin being in a range of about 20% to 50% by weight of the non-water ingredients of the aqueous coating suspension, the plasticizer being in a range of about 5% to 10% by weight of the non-water ingredients of the aqueous coating suspension, the detackifier being in a range of greater than 0% to about 10% by weight of the non-water ingredients of the aqueous coating suspension, the secondary film former being in a range of greater than 0% to 5% by weight of the non-water ingredients of the aqueous coating suspension, the flow aid being in a range of greater than 0% to about 10% by weight of the non-water ingredients of the aqueous coating suspension, and the colorant being in a range of greater than 0% to about 20% by weight of the non-water ingredients of the aqueous coating suspension, the maltodextrin having an average molecular weight less than about 27,000, the cellulosic polymer being selected from the group consisting of methylcellulose, hydroxypropyl cellulose, hydroxypropyl methylcellulose, hydroxyethyl cellulose, and carboxymethylcellulose, the plasticizer being selected from the group consisting of polyethylene glycol, triacetin, propylene glycol, acetyltriethyl citrate, triethyl citrate, and glycerin, the detackifier being selected from the group consisting of lecithin and stearic acid, the secondary film former being selected from the group consisting of sodium alginate, propylene glycol alginate, and polyvinylpyrrolidone, the flow aid being selected from the group consisting of talc, fumed silica, bentonite, edible hydrogenated vegetable oils, and hydrogenated vegetable oil and waxes, the colorant being selected from the group consisting of FD&C lakes, D&C lakes, titanium dioxide and dyes, and spraying an effective amount of said coating suspension onto said substrates to form a film coating of the film former on said substrates, and drying the film coating on said substrates.

32. A method of coating substrates from the group consisting of pharmaceutical tablets, food and confectionery forms, and agricultural seeds, with a protective film comprising the steps of mixing a film former, the film former including a film forming amount of cellulosic polymer and a film forming amount of maltodextrin, a plasticizer, a detackifier, a secondary film former, a flow aid, and a colorant into water to form an aqueous coating suspension, the cellulosic polymer being in a range of greater than 5% to about 90% by weight of the non-water ingredients of the aqueous coating suspension, the maltodextrin being in a range of about 5% to 78.5% by weight of the non-water ingredients of the aqueous coating suspension, the plasticizer being in a range of about 2.5% to 20% by weight of the non-water ingredients of the aqueous coating suspension, the detackifier being in a range of greater than 0% to about 15% by weight of the non-water ingredients of the aqueous coating suspension, the secondary film former being in a range of greater than 0% to about 10% by weight of the non-water ingredients of the aqueous coating suspension, the flow aid being in a range of greater than 0% to about 20% by weight of the non-water ingredients of the aqueous coating suspension, and the colorant being in a range of greater than 0% to about 30% by weight of the non-water ingredients of the aqueous coating suspension, the maltodextrin having an average molecular weight of less than about 27,000, the cellulosic polymer being selected from the group consisting of methylcellulose, hydroxypropyl cellulose, hydroxypropyl methylcellulose, hydroxyethyl cellulose, and carboxymethylcellulose, the plasticizer being selected from the group consisting of polyethylene glycol, triacetin, propylene glycol, acetyltriethyl citrate, triethyl citrate, and glycerin, the detackifier being selected from the group consisting of lecithin and stearic acid, the secondary film former being selected from the group consisting of sodium alginate, propylene glycol alginate, and polyvinylpyrrolidone, the flow aid being selected from the group consisting of talc, fumed silica, bentonite, edible hydrogenated vegetable oils, and hydrogenated vegetable oil and waxes, the colorant being selected from the group consisting of FD&C lakes, D&C lakes, titanium dioxide and dyes and spraying an effective amount of said coating suspension onto said substrates to from a film coating of the film former on said substrates, and drying the film coating on said substrates.

33. A coated substrate produced by the method of claim 8.

34. The method of claim 1, including dispersing a functional additive into the aqueous coating suspension.

35. A coated substrate produced by the method of claim 10.

36. A coated substrate produced by the method of claim 11.

37. A method of coating substrates from the group consisting of pharmaceutical tablets, food and confectionery forms, and agricultural seeds, with a protective film comprising the steps of forming an aqueous coating suspension consisting essentially of cellulosic polymer, maltodextrin, plasticizer, and water, the cellulosic polymer being in a range of greater than 5% to about 90% by weight of the non-water ingredients of the aqueous coating suspension, the maltodextrin being in a range of about 5% to about 78.5% by weight of the non-water ingredients of the aqueous coating suspension, and the plasticizer being in a range of about 2.5% to about 20% by weight of the non-water ingredients of the aqueous coating suspension, spraying an effective amount of said coating suspension onto said substrates to form a film coating of the film former on said substrates, and drying the film coating on said substrates.

38. A coated substrate produced by the method of claim 13.

39. A coated substrate produced by the method of claim 14.

40. A method of making a dry edible film coating composition for use in coating pharmaceutical tablets, food and confectionery forms, and agricultural seeds, with a protecting film, comprising the steps of mixing a film former, the film former including a film forming amount of cellulosic polymer and a film forming amount of maltodextrin, to form a cellulosic-maltodextrin polymer mix, and adding a plasticizer to the cellulosic polymer-maltodextrin mix and mixing until the combined mix is blended to form the dry edible film coating composition, the cellulosic polymer being in a range of greater than 5% to about 90% by weight of the dry edible film coating composition, the maltodextrin being in a range of about 5% to about 78.5% by weight of the dry edible film coating composition, and the plasticizer being in a range of about 2.5% to about 20% by weight of the dry edible film coating composition, further including adding a secondary film former to the mix and mixing until the combined mix is blended to form the dry edible film coating composition.

41. A coated substrate produced by the method of claim 16.

42. A coated substrate produced by the method of claim 17.

43. The method of claim 40, wherein the secondary film former is selected from the group consisting of sodium alginate, propylene glycol alginate, and polyvinylpyrrolidone.

44. A coated substrate produced by the method of claim 19.

45. A coated substrate produced by the method of claim 20.

46. The method of claim 40, wherein the secondary film former is in a range of 0% to 10% by weight of the combined mix.

47. A coated substrate produced by the method of claim 22.

48. The method of claim 40, wherein the secondary film former is in a range of 0% to 5% by weight of the combined mix.

49. A method of making a dry edible film coating composition for use in coating pharmaceutical tablets, food and confectionery forms, and agricultural seeds, with a protecting film, comprising the steps of mixing a film former, the film former including a film forming amount of cellulosic polymer and a film forming amount of maltodextrin, to form a cellulosic-maltodextrin polymer mix, and adding a plasticizer to the cellulosic polymer-maltodextrin mix and mixing until the combined mix is blended to form the dry edible film coating composition, the cellulosic polymer being in a range of greater than 5% to about 90% by weight of the dry edible film coating composition, the maltodextrin being in a range of about 5% to about 78.5% by weight of the dry edible film coating composition, and the plasticizer being in a range of about 2.5% to about 20% by weight of the dry edible film coating composition, further including adding a detackifier to the mix and mixing until the combined mix is blended to form the dry edible film coating composition, wherein the detackifier is lecithin or stearic acid.

50. A coated substrate produced by the method of claim 25.

51. The method of claim 49, wherein the detackifier is in a range of 0% to 15% by weight of the combined mix.

52. The method of claim 49, wherein the detackifier is in a range of 0% to 10% by weight of the combined mix.

53. A dry powder edible film coating composition for use in coating pharmaceuticals, food, confectionery forms, and agricultural seeds, comprising a dry mixture of a film former, the film former including a film forming amount of cellulosic polymer and a film forming amount of maltodextrin, the cellulosic polymer being greater than 5% to about 90% by weight of the coating composition, the maltodextrin being about 5% to about 78.5% by weight of the coating composition, and a plasticizer, the plasticizer being about 2.5% to about 20% by weight of the composition, further including a secondary film former.

54. A dry powder edible film coating composition for use in coating pharmaceuticals, food, confectionery forms, and agricultural seeds, comprising a dry mixture of a film former, the film former including a film forming amount of cellulosic polymer and a film forming amount of maltodextrin, the cellulosic polymer being greater than 5% to about 90% by weight of the coating composition, the maltodextrin being about 5% to about 78.5% by weight of the coating composition, and a plasticizer, the plasticizer being about 2.5% to about 20% by weight of the composition, further including a colorant, wherein the colorants are in a range of 0% to 20% by weight of the composition.

55. A dry powder edible film coating composition for use in coating pharmaceuticals, food, confectionery forms, and agricultural seeds, comprising a dry mixture of a film former, the film former including a film forming amount of cellulosic polymer and a film forming amount of maltodextrin, the cellulosic polymer being greater than 5% to about 90% by weight of the coating composition, the maltodextrin being about 5% to about 78.5% by weight of the coating composition, and a plasticizer, the plasticizer being about 2.5% to about 20% by weight of the composition, further including a colorant, wherein said colorants are in a range of 0% to 30% by weight of the composition.

56. A dry powder edible film coating composition for use in coating pharmaceuticals, food, confectionery forms, and agricultural seeds, comprising a dry mixture of a film former, the film former including a film forming amount of cellulosic polymer and a film forming amount of maltodextrin, the cellulosic polymer being greater than 5% to about 90% by weight of the coating composition, the maltodextrin being about 5% to about 78.5% by weight of the coating composition, and a plasticizer, the plasticizer being about 2.5% to about 20% by weight of the composition, further including a colorant, wherein said colorants are FD&C lakes, D&C lakes, titanium dioxide or dyes.

57. The dry edible film coating composition of claim 53, wherein the secondary film former is in a range of 0% to 10% by weight of the composition.

58. The dry edible film coating composition of claim 53, wherein the secondary film former is in a range of 0% to 5% by weight of the composition.

59. A dry powder edible film coating composition for use in coating pharmaceuticals, food, confectionery forms, and agricultural seeds, comprising a dry mixture of a film former, the film former including a film forming amount of cellulosic polymer and a film forming amount of maltodextrin, the cellulosic polymer being greater than 5% to about 90% by weight of the coating composition, the maltodextrin being about 5% to about 78.5% by weight of the coating composition, and a plasticizer, the plasticizer being about 2.5% to about 20% by weight of the composition, further including a detackifier, wherein the detackifier is lecithin or stearic acid.

60. The dry edible film coating composition of claim 59, wherein the detackifier is in a range of 0% to 15% by weight of the composition.

61. The dry edible film coating composition of claim 59, wherein the detackifier is in a range of 0% to 10% by weight of the composition.

62. The dry edible film coating composition of claim 53, wherein the secondary film former is selected from the group consisting of sodium alginate, propylene glycol alginate, and polyvinylpyrrolidone.

* * * * *